US012082544B2

(12) United States Patent
Khayat

(10) Patent No.: US 12,082,544 B2
(45) Date of Patent: Sep. 10, 2024

(54) **METHOD FOR PRODUCING BANANA PLANTS WITH TOLERANCE TO *FUSARIUM OXYSPORUM CUBENSIS* TR4**

(71) Applicant: RAHAN MERISTEM (1998) LTD, Western Galilee (IL)

(72) Inventor: Eli Khayat, Nahariya (IL)

(73) Assignee: RAHAN MERISTEM (1998) LTD, Western Galilee (IL)

(*) Notice: Subject to any disclaimer, the term of this patent is extended or adjusted under 35 U.S.C. 154(b) by 0 days.

(21) Appl. No.: 16/647,268

(22) PCT Filed: Sep. 13, 2018

(86) PCT No.: PCT/IL2018/051029
§ 371 (c)(1),
(2) Date: Mar. 13, 2020

(87) PCT Pub. No.: WO2019/053720
PCT Pub. Date: Mar. 21, 2019

(65) Prior Publication Data

US 2020/0275624 A1 Sep. 3, 2020

Related U.S. Application Data

(60) Provisional application No. 62/558,463, filed on Sep. 14, 2017.

(51) Int. Cl.
*A01H 5/08* (2018.01)
*A01H 1/06* (2006.01)
*A01H 6/00* (2018.01)

(52) U.S. Cl.
CPC ................. *A01H 1/06* (2013.01); *A01H 6/00* (2018.05)

(58) Field of Classification Search
None
See application file for complete search history.

(56) References Cited

U.S. PATENT DOCUMENTS

2006/0143740 A1 6/2006 Khayat

FOREIGN PATENT DOCUMENTS

| | | | |
|---|---|---|---|
| CN | 104335902 | A | 2/2015 |
| JP | 2008-187967 | A | 8/2008 |
| WO | 2006/067785 | A1 | 6/2006 |
| WO | 2017093317 | A1 | 6/2017 |

OTHER PUBLICATIONS

Madlung et al. "Remodeling of DNA Methylation and Phenotypic and Transcriptional Changes in Synthetic *Arabidopsis* Allotetraploids". Plant Physiology. 129: 733-746. 2002 (Year: 2002).*

Kadota and Niimi. "Effects of cytokinin types and their concentrations on shoot proliferation and hyperhydricity in in vitro pear cultivar shoots". Plant Cell, Tissue and Organ Culture. 72: 261-265. 2003 (Year: 2003).*

Molina, et al. "Field resistance of Cavendish somaclonal variants and local banana cultivars to tropical race 4 of Fusarium wilt in the Philippines". ISHS Acta Horticulturae 1114: XXIX: IX. 227-230. (Year: 2004).*

Khayat et al. Banana Improvement: Cellular, Molecular Biology and Induced mutations. Chapter 9, "Somaclonal variation in banana (*Musa acuminata* cv. Grande Naine).Genetic mechanism, frequency, and application as a tool for clonal selection". Food and Agriculture Organization (Year: 2004).*

Bucher, et al. "Epigenetic control of transposon transcription and mobility in *Arabidopsis*". Current Opinion in Plant Biology. 15: 503-510 (Year: 2012).*

Liu et al. "Activation of a rice endogenous retrotransposon Tos17 in tissue culture is accompanied by cytosine demethylation and causes heritable alteration in methylation pattern of flanking genomic regions". Theor Appl Genet. 109(1):200-209. (Year: 2004).*

Teo et al. "Genome Constitution and Classification Using Retrotransposon Based Markers in the Orphan Crop Banana". Journal of Plant Biology. 48(1): 96-105. (Year: 2005).*

Akimoto et al., "Epigenetic Inheritance in Rice Plants", Annals of Botany, 2007, vol. 100, pp. 205-217.

Bucher et al., "Epigenetic control of transposon transcription and mobility in *Arabidopsis*", Current Opinion in Plant Biology, 2012, vol. 15, pp. 503-510.

Cavrak et al., "How a Retrotransposon Exploits the Plant's Heat Stress Response for Its Activation", PLoS Genet, 2014, vol. 10, No. 1, e1004115, 12 pages.

Chai et al., "Biotechnology and in vitro mutagenesis for banana improvement", Banana improvement-cellular, molecular biology and induced mutation. Enfield, NH, USA: FAO/IAEA/INIBAP, Science Publishers Inc, 2004, pp. 59-77.

Dita et al., "A molecular diagnostic for tropical race 4 of the banana fusarium wilt pathogen", Plant Pathology, 2010, vol. 59, Issue 2, pp. 348-357.

Khayat et al., "Somaclonal Variation in Banana (*Musa acuminata* cv. Grande Name), Genetic Mechanism, Frequency, and Application as a Tool for Clonal Selection", Science Publishers Inc, 2004, pp. 97-109, XP002373285.

(Continued)

*Primary Examiner* — Matthew R Keogh
*Assistant Examiner* — David R Byrnes
(74) *Attorney, Agent, or Firm* — BROWDY AND NEIMARK, PLLC

(57) ABSTRACT

Provided is a method for producing a banana plant with tolerance or resistance to *Fusarium oxysporum Cubensis* TR4 and such plants. The method includes (a) exposing one or more banana meristems, in one or more propagating cycles, to a medium including a demethylating agent (in vitro mutagenesis) to thereby provide one or more banana meristems exhibiting expression and thereby amplification of retrotransposable elements in their plant genome as determined by Southern blot hybridization analysis, and (b) rooting the meristems that exhibited the amplification and regenerating therefrom one or more regenerated banana plants, at least one of the regenerated banana plants having tolerance or resistance to *Fusarium oxysporum Cubensis* TR4.

9 Claims, 7 Drawing Sheets

Specification includes a Sequence Listing.

(56) References Cited

OTHER PUBLICATIONS

Kim et al., "DNA methylation as a system of plant genomic immunity", Trends in Plant Science, 2014, vol. 19, No. 5, pp. 320-326.
Le et al., "DNA demethylases target promoter transposable elements to positively regulate stress responsive genes in *Arabidopsis*", Genome Biology, 2014, vol. 15, pp. 458 (18 Pages).
Matsunaga et al., "A small RNA mediated regulation of a stress-activated retrotransposon and the tissue specific transposition during the reproductive period in *Arabidopsis*", Frontiers in Plant Science, Plant Physiology, 2015, vol. 6, Article 48, 12 Pages.
Molina et al., "Varietal Resistance Evaluation of Cavendish Somaclones to Fusarium Wilt caused by *Fusarium oxysporum* f.sp. *cubense*, Tropical Race 4", Bioversity International, 2012, 1 Page, XP55521984.
Perez-Vicente et al., "Technical Manual: Prevention and diagnostic of Fusarium Wilt (Panama disease) of banana caused by *Fusarium oxysporum* f. sp. *cubense* Tropical Race 4 (TR4)", Food and Agriculture Organization of the United Nations, 2014, 74 Pages. (Split Into Five Segments).
Saze et al., "DNA Methylation in Plants: Relationship to Small RNAs and Histone Modifications, and Functions in Transposon Inactivation", Plant Cell Physiol., 2012, vol. 53, No. 5, pp. 766-784.
Teo et al., "The Cloning of Ty1-copia-like Retrotransposons from 10 Varieties of Banana (*Musa* Sp.)", Journal of Biochemistry, Molecular Biology and Biophysics, 2002, vol. 6, No. 3, pp. 193-201.
Wei et al., "The effect of transposable elements on phenotypic variation: insights from plants to humans", Science China: Life Sciences, 2016, vol. 59, No. 1, pp. 24-37.
Zou et al., "Retrotransposons—a Major Driving Force in Plant Genome Evolution and a Useful Tool for Genome Analysis", J. Crop Sci. Biotech., 2009, vol. 12, No. 1, pp. 1-8.
Arinaitwe et al., "Proliferation rate effects of cytokinins on banana (*Musa* spp.) cultivars", Scientia Horticulturae, 86 (2000) 13-21.
Gubbuk et al, "In Vitro Propagation of Some New Banana Types (*Musa* spp.)", Turk J Agric For, 28 (2004) 355-361.
Dale et al., "Transgenic Cavendish bananas with resistance to Fusarium wilt tropical race 4", 2017; Nature Communications 8: 1496.
Deleris et al., "DNA Methylation and Demethylation in Plant Immunity", Annu. Rev. Phytopathol., 2016, 54:579-603.
Li et al., "Resistance sources to *Fusarium oxysporum* f. sp. *cubense* tropical race 4 in banana wild relatives", Plant Pathology, 2014, 7 pages.
Hwang et al., Cavendish Banana Cultivars Resistant to Fusarium Wilt Acquired through Somaclonal Variation in Taiwan, The American Phytopathological Society, Plant Disease, 88(6):580-588 (2004).
Zhu et al., Controlling integration specificity of a yeast retrotransposon, PNAS, 100(10):5891-5895 (2003).

* cited by examiner

METHOD FOR PRODUCING BANANA PLANTS WITH TOLERANCE TO *FUSARIUM OXYSPORUM CUBENSIS* TR4

TECHNOLOGICAL FIELD

The present disclosure relates to plant resistance and in particular to a method of producing plants with tolerance or resistance to *Fusarium oxysporum Cubensis* TR4.

BACKGROUND ART

References considered to be relevant as background to the presently disclosed subject matter are listed below:

Chai, M., et al. "*Biotechnology and in vitro mutagenesis for banana improvement*." Banana improvement-cellular, molecular biology and induced mutation. Enfield, NH, USA: FAO/IAEA/INIBAP, Science Publishers Inc, 2004, 59-77.

Akimoto, Keiko, et al. "*Epigenetic inheritance in rice plants*." Annals of botany 100.2 (2007): 205-217.

Luis Pérez-Vicente et al. "*Technical Manual, Prevention* and *diagnostic of Fusarium Wilt* (*Panama disease*) *of banana caused by Fusarium oxysporum f. sp. cubense* Tropical Race 4 (*TR*4)" FOOD AND AGRICULTURE ORGANIZATION OF THE UNITED NATIONS, May 2014

Dita, M. A., et al. "*A molecular diagnostic for tropical race* 4 *of the banana fusarium wilt pathogen." Plant Pathology* 59.2 (2010): 348-357.

Acknowledgement of the above references herein is not to be inferred as meaning that these are in any way relevant to the patentability of the presently disclosed subject matter.

BACKGROUND

Global banana production is seriously threatened by the re-emergence of a *Fusarium* Wilt. The disease, caused by the soil-borne fungus *Fusarium oxysporum* f. sp. *Cubense* (FOC) and also known as "Panama disease", wiped out the Gros Michel banana industry in Central America and the Caribbean, in the mid-twentieth century. The effects of FOC Race 1 were overcome by a shift to resistant Cavendish cultivars, which are currently the source of 99% of banana exports. More than 80% of global banana and plantain production is thought to be based on TR4 susceptible germplasm. This strain of FOC has caused epidemics in Cavendish in the tropics different from those less-severe infections previously reported in the sub-tropics. [Luis Pérez-Vicente et al. "Technical Manual, Prevention and diagnostic of *Fusarium* Wilt (Panama disease) of banana caused by *Fusarium oxysporum* f. sp. *cubense* Tropical Race 4 (TR4)" FOOD AND AGRICULTURE ORGANIZATION OF THE UNITED NATIONS, May 2014]

*Fusarium oxysporum* f sp. *Cubense* spores can lie dormant in the soil for even 30 years. The spores infect a susceptible plant through the roots and colonize the plant's xylem vessels, blocking the flow of water and nutrients. This condition produces the symptoms called *Fusarium* wilt. The characteristic symptom of *Fusarium* wilt is blackened, discoloured and weakened vascular tissue within the stems of the plant. The discolouration varies from pale yellow in the early stages to dark red and black in the later stages. Internal symptoms initially develop in the feeder roots and rhizomes and then in the plant's pseudostem.

Currently, they are resistant to fungicides and cannot be eliminated from the soil by any chemical treatment. Thus, hitherto, there is no viable fully effective treatment of soil or plants to control or cure *Fusarium* wilt in the field.

Chai, M., et al. initiated a program for improving banana cultivars by induced mutations. Pisang Berrangan (AAA) banana plant was gamma-irradiated at various dosages. Mutants tolerant to *Fusarium* wilt were selected [Chai, M., et al. "*Biotechnology and in vitro mutagenesis for banana improvement*." Banana improvement-cellular, molecular biology and induced mutation. Enfield, NH, USA: FAO/IAEA/INIBAP, Science Publishers Inc, 2004, 59-77].

Akimoto, Keiko, et al show that demethylation activated a disease resistance gene in rice plant [Akimoto, Keiko, et al. "*Epigenetic inheritance in rice plants*." Annals of botany 100.2 (2007): 205-217].

Luis Pérez-Vicente et al. reviewed main aspects of *Fusarium* wilt and disclosed different protocols regarding the sampling, extraction, and isolation storage, banana inoculation, and molecular extraction and diagnostic tools [Luis Pérez-Vicente et al. "*Technical Manual, Prevention* and *diagnostic of Fusarium Wilt* (*Panama disease*) *of banana caused by Fusarium oxysporum f. sp. cubense Tropical Race* 4 (*TR*4)" FOOD AND AGRICULTURE ORGANIZATION OF THE UNITED NATIONS, May 2014].

Dita, M. A., et al. discloses a rapid TR4 detection method that is based on PCR and can be applied in planta. [Dita, M. A., et al "*A molecular diagnostic for tropical race* 4 *of the banana fusarium wilt pathogen." Plant Pathology* 59.2 (2010): 348-357]

GENERAL DESCRIPTION

The present disclosure provides, in accordance with a first of its aspects, a method for producing a banana plant with tolerance to *Fusarium oxysporum Cubensis* TR4 the method comprising:

(a) exposing one or more banana meristems, in one or more propagating cycles, to a medium comprising a demethylating agent to thereby provide one or more banana meristems exhibiting expression and thereby amplification of retrotransposable elements in their plant genome as visualized by Southern blot hybridization analysis;

(b) rooting said meristems that exhibited said amplification and regenerating therefrom one or more regenerated banana plants, at least one of said regenerated banana plants having tolerance or resistance to *Fusarium oxysporum Cubensis.*

In accordance with a second aspect, the present disclosure provides a banana plant comprising at least one genomic marker associated with the plant's tolerance or resistance to *Fusarium oxysporum Cubensis* TR4, said tolerance or resistance being exhibited by a banana plant remaining asymptomatic after exposure with *Fusarium oxysporum Cubensis* TR4.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2A shows no significant symptoms of the disease, while FIGS. 2B-2E) show typical and advanced symptoms of the disease.

DETAILED DESCRIPTION OF EMBODIMENTS

Figure 1:
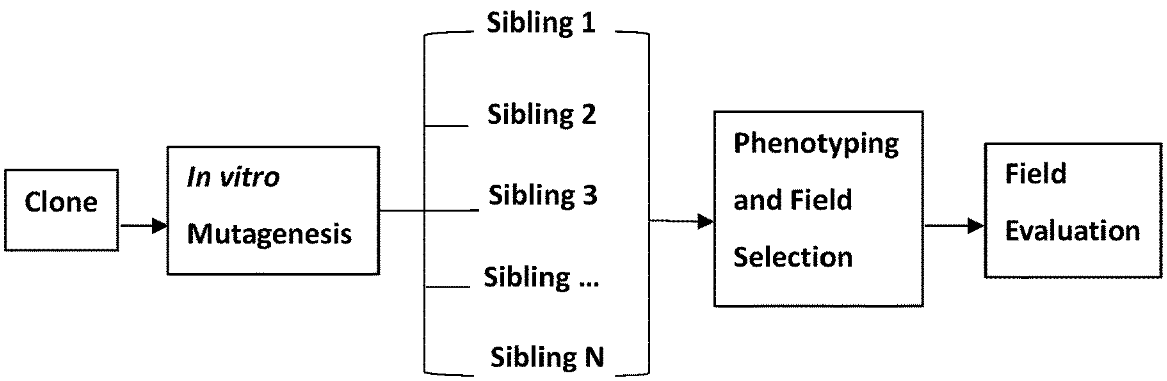
FIG. 1 is a block diagram describing a method producing a banana plant with tolerance or resistance to *Fusarium oxysporum Cubensis* TR4, in accordance with an embodiment of the present disclosure.

The present invention is based on the finding that exposing banana plant meristems to a demethylating agent during 1-2 propagation cycles in the micropropagation stage of cultivation produced a plurality of mutant Cavendish banana plants, among which some exhibited resistance to *Fusarium oxysporum Cubensis* TR4 pathogen.

Based on the above finding, a method of producing Cavendish banana plants with tolerance or resistance to *Fusarium oxysporum Cubensis* and specifically to *Fusarium oxysporum Cubensis* TR4 has been established.

*Fusarium oxysporum Cubensis* is a typical vascular wilt disease that produces various symptoms called *Fusarium* wilt. The symptoms can be divided into internal symptoms and external symptoms.

The characteristic internal symptom of *Fusarium* wilt is vascular discolouration, which varies from pale yellow in the early stages to dark red or almost black in later stages. Internal symptoms first develop in the feeder roots, which are the initial infection sites. The fungus spreads to the rhizome and then to the pseudostem.

External symptoms include wilting and yellowing of older leaves around the margins. The yellow leaves may remain erect or collapse at the petiole. Eventually, all the leaves fall down and dry up. Another common symptom is the splitting of the base of the pseudostem. Other symptoms include irregular, pale margins on new leaves and the wrinkling and distortion of the leaf blade.

Thus, in the context of the present disclosure, when referring to tolerance, it is to be understood that the plant is infected by the fungus, but remains viable and productive in terms of fruit yield. In this respect, the plant may or may not show one or more symptoms of the disease. In some embodiments, the plant does not show external symptoms of the disease, yet exhibit internal symptoms of the disease. In some other embodiments, the plant shows mild symptoms (external and/or internal) of the disease, but still remains viable.

Further, in the context of the present disclosure, when referring to resistance, it is to be understood that the plant does not show any of the characteristic symptoms, that is remains asymptomatic, of the disease.

The method disclosed herein is for producing one or more mutant banana plants with tolerance or resistance to *Fusarium oxysporum Cubensis* TR4.

In some embodiments, the tolerance or resistance is determined by the absence of one or more symptoms of the disease. In some embodiments, the one or more symptoms include at least one of, at times a combination of leaves wilting, leaves yellowing and blackening of the plant's vascular system.

Specifically, the method disclosed herein for producing banana plants with tolerance or resistance to *Fusarium oxysporum Cubensis* TR4 comprises:

(a) exposing one or more banana meristems, in one or more propagating cycles, to a medium comprising a demethylating agent to thereby provide one or more banana meristems exhibiting expression and thereby amplification of retrotransposable elements in their plant genome as determined by Southern blot hybridization analysis, (b) rooting said meristems that exhibited said amplification and regenerating therefrom one or more regenerated banana plants, at least one of said regenerated banana plants having tolerance or resistance to *Fusarium oxysporum Cubensis* TR4.

The banana meristem explants employed by the method of the present disclosure is typically, but not exclusively, a shoot apical meristem. The banana meristem explant is placed in a culture media and is allowed to propagate.

As appreciated, the propagation is required in order to multiply the number of cells from the same single explant. The multiplication process involves a plurality of micropropagation cycles, each cycle involving replacement of the culture media. Typically, the culture media contain, at minimum, inorganic salts, nutrients, growth regulators (Auxins and Cytokinin), complex natural preparations and inert supportive materials. Each cycle does not necessarily use the same culture media as the previous one, and the type of culture media or any supplements added to a culture media will depend on the particular stage of the meristem propagation.

Banana meristems are typically cultured by employing a plurality of propagation cycles. According to the present disclosure, at least one, at times, 1-3 propagation cycles are in a medium comprising a demethylating agent. The exposure to the medium comprising the demethylating agent is after sufficient multiplication of the meristematic cells in the culture.

In the context of the present disclosure, when referring to a demethylating agent it is to be understood as an agent comprising one or a combination of compounds that inhibits nucleic acid methylation. In some embodiments the compound is a DNA methyltransferase inhibitor. A non-limiting list of DNA methyltransferase inhibitor include azacitidine and 5-aza-2'-deoxycytidine (decitabine).

In some preferred embodiments, the demethylation agent comprises decitabine. In some embodiments the amount of decitabine is between 0.1-50 μM.

In some preferred embodiments, the demethylation agent comprises decitabine. In some embodiments the amount of decitabine is any one of 1, 10, 15, 30, or 45 μM, each amount representing a different embodiment of the invention.

In some preferred embodiments, the demethylation agent comprises decitabine. In some embodiments the amount of decitabine is 30 μM.

Exposure of the propagating meristems to a demethylation agent typically takes place after at least 10 propagating cycles. In some embodiments, the exposure to a media supplemented with the demethylating agent is after at least 15 propagating cycles.

The exposure to the demethylating agent may be in a single propagating cycle, but also in more than one propagating cycles. In some embodiments, the exposing of the one or more meristems to the demethylating agent in for at least two, typically sequential, propagating cycles. A determination on how many cycles need to be in the presence of the demethylating agent can be based on the level of expression and thereby amplification of retrotransposable elements in their plant genome, as determined by Southern blot hybridization analysis, as further discussed below.

In some embodiments, during the propagation stage, and typically before exposure to the demethylating agent, the meristematic tissues are propagated, at least in one propagating cycle, in a media comprising a cytokinin-like substance. Cytokinin like substances are known in the art, and non-limiting examples, include isopentenyl adenine (2iP), kinetin (KIN), 6-Benzyladenin (BA) and 6-Benzylaminopurine (BAP), 1-phenyl-3-(1,2,3-thiadiazol-5-yl) urea (TDZ).

In one preferred embodiment, the cytokinin-like substance is TDZ, which was found to provide the best rate of multiplication.

The presence of TDZ in the culture media is in very low amounts, typically, in the range of 0.1 ppm. This amount is sufficient to induce the desired cell division.

The next stage in the disclosed method involves rooting of the meristems that exhibit a desired level of retro-transposable elements expression. As indicated above, the level of expression can be determined by Southern blot hybridization analysis. In one embodiment, the expression and amplification is determined to be sufficient when the level reached a plateau.

As appreciated, retro-transposable elements (or retrotransposons, or RT) are DNA sequences that undergo transcription into RNA and are subsequently converted back to DNA sequences which are is inserted back into the genome. The increase in expression (the amplification) of the retro-transposable elements is indicative of the increase in the number of copies of the sequence inserted back into the genome.

The expression and amplification of the retrotransposons can be determined by various DNA detection techniques, for example, by Southern blot hybridization.

Various probes can be utilized in Southern blot hybridization analysis of retrotransposons. These include, for example, probes specific to retrotransposons, for example, Ban-1, a portion of the gene encoding the reverse transcriptase of Copia 1 retro-transposable element.

The sequence of Ban-1 is provided below and is referred to as SEQ ID NO:1:

```
ggaggaggat gtatatgatg caacctgagg gattcatgtc

caagaactgc ccagataagg tgtgtaggtt gcttagatcc

atttagggac taaagcaagc ttcccgaagt tggaacataa

gatttgatga ggcaatcaga tcttatgact tcgttaagaa
```

-continued

```
cgaagatgag ccttgtgtat acagaaaggt aagtgggagc

gctattagct ttttggtgtt atatgtagat gacatcctcg

tctttgggaa tgacatagga atgctatcca caataaaggc

ttggttatct agacacttct ccatgaagg
```

To perform the Southern blot analysis, a sample of DNA is taken from the culture medium. To verify when the expression and reached the desired level, samples can be taken from sequential proliferation cycles, each time being subjected to Southern blot analysis and once the desired level is determined, the method can go forward to the next stage.

Methods for propagation and rooting are known in the art, for example, as described in Cronauser S. S. et al.: *Annuls of Botany* 53 (1984) 321-328. Generally, the plants are placed in a rooting and regeneration medium, optionally Murashige and Skoog (MS) medium, for a time sufficient to obtain the regenerated plant. [Murashige, T. and F. Skoog. 1962. A revised medium for rapid growth and bioassays with tobacco tissue cultures. Physiol. Plant. 15: 473-497.]

Once clusters of plants (plants originating from the same plant in the previous cycle, and typically, 5-8 plants per sibling cluster) are developed, these are separated for hardening and planting. As appreciated, hardening is a process of exposing the plants, after tissue culture, to environmental conditions that will keep them at high humidity and mild temperature so that they do not suffer from a shock once they are exposed to the "harsh" ambient conditions. As further appreciated, planting can be in the open field or in a greenhouse.

In some embodiments, the plants tolerant or resistant to *Fusarium oxysporum Cubensis* TR4 are selected. This can be done by known selection techniques.

Typically, the selection and screening of those regenerated plants tolerant or resistant to *Fusarium oxysporum Cubensis* TR4 is performed by inoculation (exposing) the plants to an inoculum containing *Fusarium oxysporum Cubensis* TR4 spores and visually analyzing the plants after further growth. Those plants that are identified as asymptomatic are then further used for establishing the next tolerant/resistant plant generation (tissue culturing and plant regeneration).

FIG. 1 provides a block diagram of steps for obtaining banana plants according to one embodiment of the present disclosure. Specifically, a clone from banana meristem is used as a starting point for the in vitro mutagenesis. The clone is typically produced from a meristem of a banana of commercial interest (e.g. having high fruit yield etc). The clone is then subjected to the in vitro mutagenesis step, where the clone is exposed to a medium comprising a demethylating agent to thereby provide several siblings (siblings 1 to N) some of which exhibit expression and thereby amplification of retrotransposable elements in their plant genome (which can be determined by Southern blot hybridization analysis). At this stage, selection for resistance to TR4 strain of *Fusarium oxysporum* f. sp. *Cubensis* is conducted as described herein, followed by field evaluation that includes, inter alia, yield, as well as any other phenotypic characteristics that may be of commercial interest, as can be determined by those versed in the art.

The banana plants disclosed herein and have unique characteristics that can also be identified in a molecular level. Specifically, the banana plants comprise at least one genomic marker associated with a plant's tolerance or resistance to *Fusarium oxysporum Cubensis* TR4. Thus, also disclosed herein is a method of identifying banana plants with tolerance or resistance to *Fusarium oxysporum Cubensis* TR4, the method comprises identifying the genomic marker that is associated with the plant's tolerance or resistance.

In the non-limiting Examples provided below, and which form part of the present disclosure, two batches were tested, in a first batch around 4500 mutant banana plants were successfully acclimatized and subsequently inoculated with the TR4 strain of *Fusarium oxysporum* f. sp. *Cubensis*. These were divided into three study groups. Out of the total number of mutated banana plants at least 153 plants (3.4%) were determined to be asymptomatic upon inoculation to the fungi's spores; and in a second batch, out of 5200 mutant plants, 262 (5.0%) were determined to be asymptomatic upon inoculation to the fungi's spores.

DETAILED DESCRIPTION AND NON-LIMITING EXAMPLES

Preparation of Meristem Culture

Twenty clones of GAL cultivar were selected in the field for high performance each clone received an accession number. Explants were put in culture according to a standard procedure.

On the $7^{th}$ cycle of propagation 0.1 ppm Thidiazuron (TDZ) was added to the medium. In cycles 20 and 21, 30 μM 5-Aza-2-Deoxycytidine (a demethylation compound) was filter sterilized and added to the medium after solidification.

Rooting and Regeneration

In cycle 22 the plants were placed on rooting and regeneration medium.

DNA Isolation and Southern Blot Analysis

DNA samples were taken from cycle 0, 5, 21, 22 and analyzed by Southern blot hybridization, probed with Ban-1.

Samples (2.5 g) of fully expanded leaf blade tissue were harvested and ground by mortar and pestle under liquid nitrogen. The samples were homogenized in 25 ml extraction buffer containing 4 percent (w/v) CTAB, 10 mM Tris-HCl pH 8, 1.4 M NaCl and 20 mM EDTA. The extracts were placed at 65 degrees centigrade for 30 min. After cooling to room temperature an equal volume of chloroform: isoamyl alcohol (20:1) was added and after 15 min. of incubation at room temperature, the mixture was centrifuged at 5000 rpm for 5 min. The supernatant was filtered through 5 layers of cheesecloth and an equal volume of ice cold iso-propanol was added to the filtrate. Following addition of NaCl to a final concentration of 0.1 M the samples were kept at −20 degrees centigrade for one hour and subsequently centrifuged for 15 min. at 11,000 rpm at 40 degrees centigrade The resulting pellet was resuspended in 3 ml of 70 percent ethyl alcohol, the mixture was centrifuged as above, and the resulting pellet was resuspended in 0.5 ml distilled water. Aliquots of ten micro g DNA were digested with EcoRI and separated on a 1.2 percent agarose gel, stained with ethidium bromide and blotted onto a Nytran membrane. Transfer of DNA and hybridization was performed according to [Sambrook J. et al.: Molecular Cloning, A laboratory Manual. Cold Spring Harbor N.Y., Coldspring Harbor Laboratory Press].

After 24 cycles, the cluster of plants (plants originating from the same plant in the previous cycle (about 5-8 plants per sibling cluster) were divided into two batches. One batch was used for evaluation in a commercial plantation in Israel and the second batch was sent to be screened for resistance at the University of Wageningen (Holland).

Selection of Banana Plant with Resistance to TR4 Strain of *Fusarium oxysporum* f Sp. *Cubensis*

The first batch of plants were planted in the field in Israel and were later evaluated for agronomic characteristics including plant height at flowering of the second cycle of fruit, number of fingers on the bunch, bunch weight finger length etc.

Detailed botanical description of the plant, which includes its general appearance, pseudostem and suckers, petiole, midrib, leaf, inflorescence and male bud, flower bract, male flower, and fruit is disclosed below. This description is based on observations of specimens grown in the Western Galilee, Israel, 20 months after planting. The plantation is at 30 m above sea level, approximately 1200 m East of the Mediterranean sea, adjacent to the town of Shlomi. The description is based on an observation of approximately 50 plants grown in a commercial plantation. Data was collected in 2012/2013. The descriptors presented herein are in accordance with and include all of the 117 international standards found in "Descriptors for Banana (*Musa* spp.)" elaborated by CIRAD/INIBAP/IPGRI. The color terminology is in accordance with The U.K.'s Royal Horticultural Society's Colour Chart, 2001. Ploidy: Triploid (AAA). Leaf habit: Drooping.

Selection and Identification of Genomic Marker Associated with TR4 Strain of *Fusarium oxysporum* f. Sp. *Cubensis*

The second in vitro plants were hardened in Holland in a greenhouse according to standard hardening protocol. After 6 weeks the plants were transferred to 1000 cc pots containing an inert medium of peat moss based medium. Six weeks later the plants were inoculated according to a procedure used routinely for selection of resistance at the UoW Holland. Approximately 9,000 clones (1-3 plants per clone) were inoculated with 200 mL of inoculum in a concentration of 1×106 spores $mL^{-1}$. In addition to the mutated plants the experiment also included 100 control plants that were inoculated and a plant from each clone was kept not inoculated. The plants were all grown in the pots for 15 weeks. The plants were examined for symptoms 13-15 weeks post inoculation. The plants were visually analyzed (yellowing and wilting of older leaves and blackening of the internal vascular system after cutting the corm 4-5 cm above ground. One hundred and fifty three clones were found Asymptomatic from the first batch (4100 clones). The asymptomatic clones were placed in tissue culture and re-propagated to a quantity of 100 plants per clone for field trial.

FIG. 1 provides a block diagram of the method of producing the banana plants as described above.

Figures 2A, 2B, 2C, 2D, 2E:
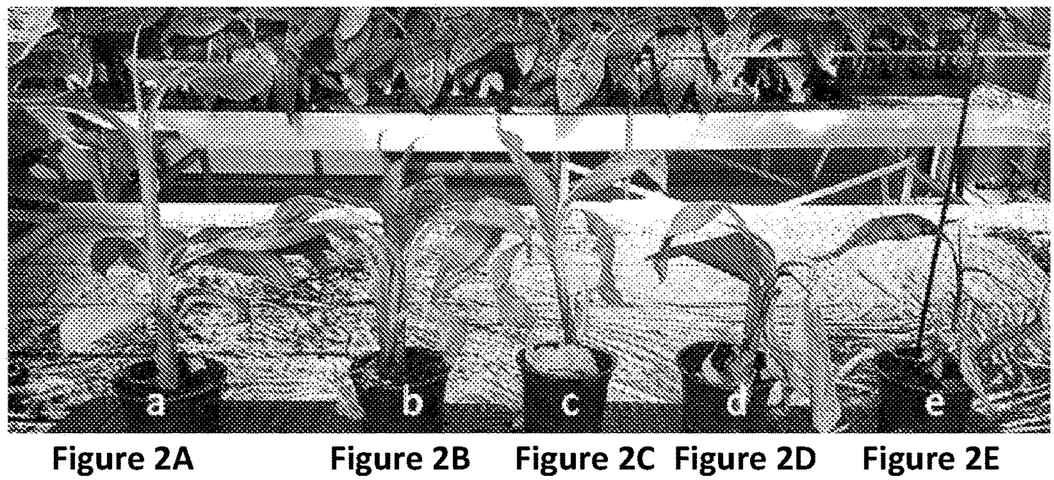
FIG. 2A-2E are images of plants 13 weeks post inoculation with the fungus pathogen where

FIGS. 2A-2E show exemplary plants 13 weeks post inoculation. Specifically, FIG. 2A is an image of a plant with no significant symptoms of the disease (this plant was thus selected for internal *Fusarium oxysporum* f. sp. *cubense* (FOC) conformation and field trials). FIGS. 2B-2E are images of plants showing more than 60% external yellowing or splitting. These plants were thus discarded.

Figure 3:
FIG. 3 is an image of a tray containing 12 inoculated banana plants, 9 weeks post inoculation with 200 ml of inoculum (concentration of $1\times10^6$ spores/ml).

FIG. 3 is an image of a tray containing 12 inoculated banana plants, 9 weeks post inoculation with 200 ml of inoculum (concentration of $1\times10^6$ spores/ml). This Figure specifically shows that that the inoculated plants were highly susceptible to the disease. The symptoms are yellowing of older leaves and wilting.

Figure 4:
FIG. 4 is an image of an asymptomatic plant 13 weeks post inoculation.

FIG. 4 is an image of an asymptomatic plant 13 weeks post inoculation. The plants do not express visual symptoms of the disease.

FIGS. 5A-5H are images of resistant (FIGS. 5A-5D) and susceptible (FIG. 5E-5F, 5H) banana plants, the resistant plants obtained according to the present disclosure. FIGS.

Figure 5A:
FIGS. 5A-5H are images of resistant (FIGS. 5A-5D, 5G) and susceptible (FIG. 5E-5F, 5H) banana plants, the resistant plants obtained according to the present disclosure, and a direct comparison between the vascular tissue within the stems of a resistant plant (FIG. 5G) and susceptible plant (FIG. 5H).
Figure 5B:
Figure 5C:
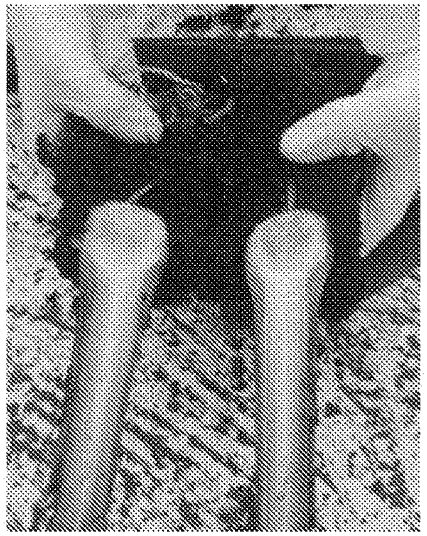
Figure 5D:
Figure 5E:
Figure 5F:
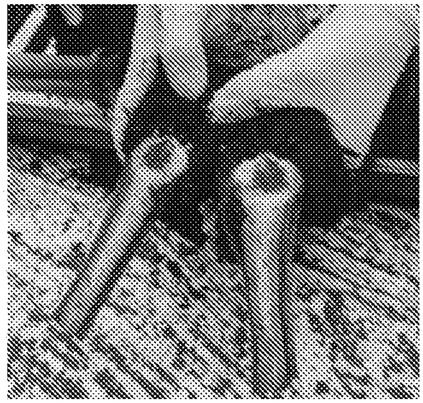
Figure 5G:
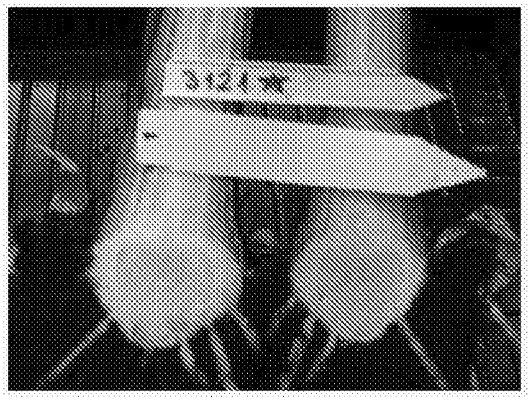
Figure 5H:
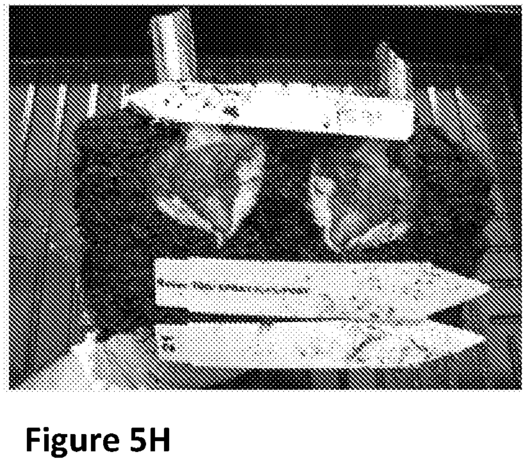
Figure 6A:
FIG. 6A-6G are images of resistant banana plants produced in accordance with the present disclosure at different stages, with FIGS. 6D-6G shown banana fruit from different siblings.
Figure 6B:
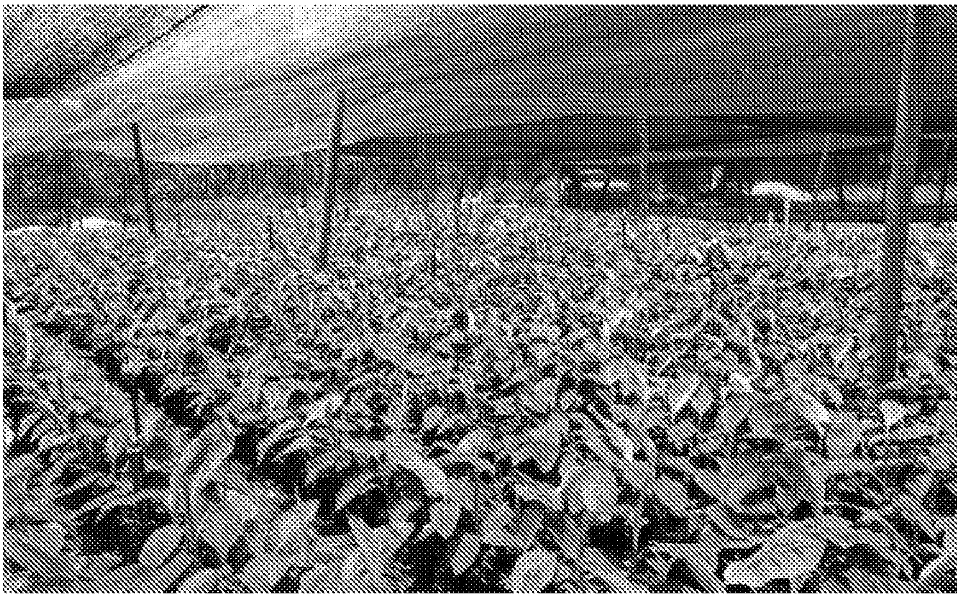
Figure 6C:
Figure 6D:
Figure 6E:
Figure 6F:
Figure 6G:

5G and 5H shows a comparison between resistant plant (FIG. 5G) obtained according to the present disclosure and susceptible plant (FIG. 5H), and blackening of the vascular tissue of the stems is shown in FIG. 5H but not in FIG. 5G.

FIGS. 6A-6G show banana plants produced by the method described herein. As shown, no disease symptoms are evident, and the plants produce high yield and commercially viable fruit.

Figure 7:
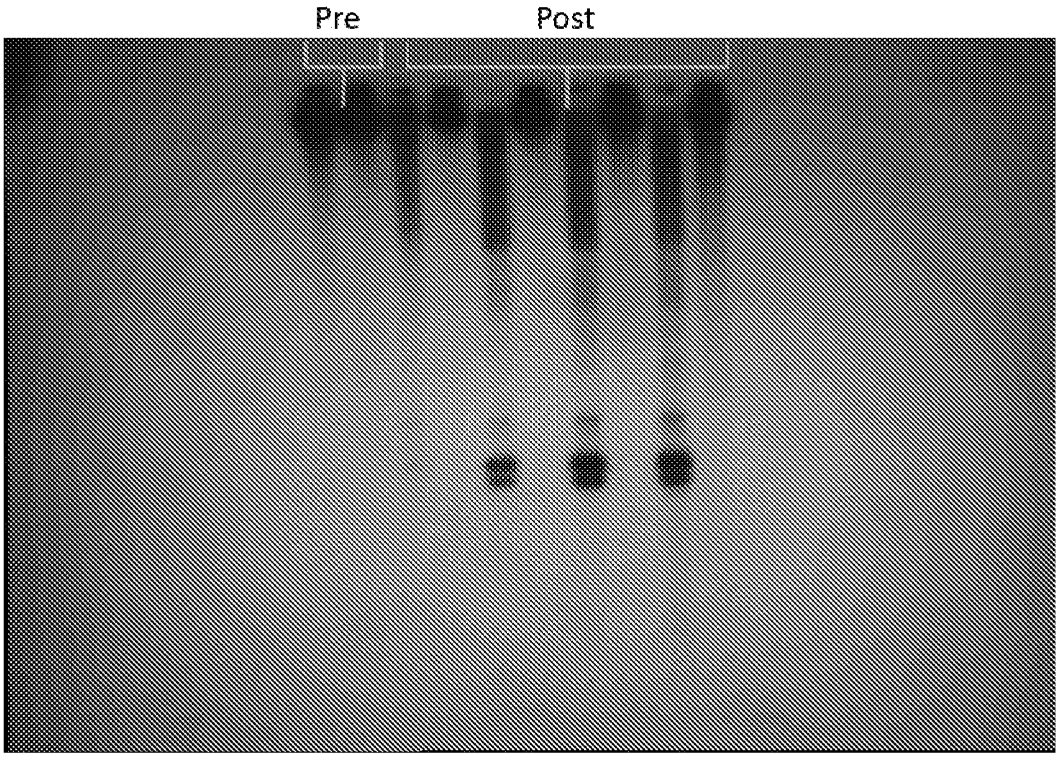
FIG. 7 is a Southern blot hybridization probed with Ban-Retro 1 probe, where pre and post indicates before or after exposure to demethylation agent, respectively.

FIG. 7 is a Southern blot hybridization probed with Ban-Retro 1 probe. Banana genomic DNA extracted from leaves of tissue cultured plants prior to the activation of retro transposable elements (lanes 1,2 marked pre) and post activation (lanes 3-10, marked post). Lanes 2, 4, 6, 8, and 10 represent genomic DNA cut with the restriction enzyme EcoR1 while lanes 1, 3, 5, 7, and 9 represent uncut DNA. The DNA fragments were hybridized with $^{32}P$ labeled Ban-Retro 1 probe. Each lane contains 10 μg of DNA. All samples shown in the figure were collected from successive cycles of tissue culture of the same explant. The banding pattern in the figure clearly reveals activation of retrotransposable elements and intensification of the elements in specific loci.

Figure 8:
FIG. 8 is putative structure of Cpia like retro-transposable element comprising: 5' long terminal repeats, 3' long terminal repeats, GAG protein, genes encoding Protease (prot.), Integrase (Intg.), Reverse transcriptase (RT), RNAs H (RN H.).

Finally, FIG. 8 provides a putative structure of Cpia like retro-transposable element comprising: 5' long terminal repeats, 3' long terminal repeats, GAG protein, genes encoding Protease (prot.), Integrase (Intg.), Reverse transcriptase (RT), RNAs H (RN H.).

The invention claimed is:

1. A method for producing a banana plant with resistance to *Fusarium oxysporum Cubensis* TR4, the method comprising: (a) exposing one or more banana meristems, in one or more propagating cycles, to a medium comprising a DNA-methyltransferase inhibitor to thereby provide one or more banana meristems exhibiting expression and thereby activation of retrotransposable elements in their plant genome; (b) rooting said meristems of (a) and regenerating therefrom one or more regenerated banana plants; (c) testing said regenerated banana plants for resistance to *Fusarium oxysporum Cubensis* TR4; and (d) selecting a regenerated banana plant testing positive for resistance to *Fusarium oxysporum Cubensis* TR4.

2. The method of claim 1, wherein said DNA-methyltransferase inhibitor is selected from the group consisting of azacitidine and-5-aza-2'-deoxycytidine.

3. The method of claim 1, wherein said DNA-methyltransferase inhibitor is 5-aza-2'-deoxycytidine.

4. The method of claim 1, comprising exposing said one or more meristems to the DNA-methyltransferase inhibitor in two or more propagating cycles.

5. The method of claim 1, wherein said one or more meristems are subjected to one or more cycles of micropropagation with 1-phenyl-3-(1,2,3-thiadiazol-5-yl) urea (TDZ) prior to exposing the same to a DNA-methyltransferase inhibitor.

6. The method of claim 1, wherein said resistance is determined by the absence of one or more of leaves wilting, leaves yellowing, blackening of the plant's vascular system.

7. The method of claim 4, wherein said exposing to said DNA-methyltransferase inhibitor is until said intensification reaches a plateau.

8. The method of claim 1, further including, after said step (d), the steps of:
(e) performing Southern blot hybridization analysis for determining the presence or absence of a genomic marker associated with resistance to *Fusarium oxysporum Cubensis* TR4, wherein said genomic marker is a banding pattern revealing activation of retrotransposable elements and intensification of said retrotransposable elements in specific genomic loci associated with resistance to *Fusarium oxysporum Cubensis* TR4; and
(f) selecting plants exhibiting the presence of said genomic marker associated with resistance to *Fusarium oxysporum Cubensis* TR4.

9. The method of claim 1, further including, after said step (a) and prior to said steps (b), (c) and (d), the steps of:
(e) performing Southern blot hybridization analysis for determining the presence or absence of a genomic marker associated with resistance to *Fusarium oxysporum Cubensis* TR4, wherein said genomic marker is a banding pattern revealing activation of retrotransposable elements and intensification of said retrotransposable elements in specific genomic loci associated with resistance to *Fusarium oxysporum Cubensis* TR4; and (f) selecting plants exhibiting the presence of said genomic marker associated with resistance to *Fusarium oxysporum Cubensis* TR4, wherein, in said step (b) the meristems that are rooted are those resulting from step (f).

* * * * *

SEQUENCE LISTING

```
<160> NUMBER OF SEQ ID NOS: 1

<210> SEQ ID NO 1
<211> LENGTH: 309
<212> TYPE: DNA
<213> ORGANISM: Artificial Sequence
<220> FEATURE:
<223> OTHER INFORMATION: Ban-1 probe

<400> SEQUENCE: 1

ggaggaggat gtatatgatg caacctgagg gattcatgtc caagaactgc ccagataagg    60

tgtgtaggtt gcttagatcc atttagggac taaagcaagc ttcccgaagt tggaacataa   120

gatttgatga ggcaatcaga tcttatgact tcgttaagaa cgaagatgag ccttgtgtat   180

acagaaaggt aagtgggagc gctattagct ttttggtgtt atatgtagat gacatcctcg   240

tctttgggaa tgacatagga atgctatcca caataaaggc ttggttatct agacacttct   300

ccatgaagg                                                           309
```